United States Patent [19]
Cordis et al.

[11] Patent Number: 5,472,443
[45] Date of Patent: Dec. 5, 1995

[54] ELECTROSURGICAL APPARATUS EMPLOYING CONSTANT VOLTAGE AND METHODS OF USE

[75] Inventors: Jack C. Cordis; Dennis J. Denen, both of Columbus; Philip E. Eggers, Dublin; John J. Knittle, Westerville; Raymond C. Ramsey, Columbus, all of Ohio; Robert F. Shaw, San Francisco, Calif.

[73] Assignee: Hemostatic Surgery Corporation, Georgetown, Cayman Islands

[21] Appl. No.: 210,090

[22] Filed: Mar. 17, 1994

Related U.S. Application Data

[63] Continuation of Ser. No. 877,533, May 1, 1992, abandoned, which is a continuation-in-part of Ser. No. 711,920, Jun. 7, 1991, abandoned.

[51] Int. Cl.⁶ ................................................. A61B 17/39
[52] U.S. Cl. ................................ 606/48; 606/49; 606/32; 606/34; 606/37
[58] Field of Search .............................. 606/27, 30, 32, 606/34, 37–42, 48–52, 205–211

[56] References Cited

U.S. PATENT DOCUMENTS

| | | |
|---|---|---|
| 1,586,645 | 6/1926 | Bierman . |
| 3,651,811 | 3/1972 | Hildebrandt et al. ............. 128/303.17 |
| 3,685,518 | 8/1972 | Beuerle et al. .................... 128/303.17 |
| 3,730,188 | 5/1973 | Ellman ............................... 128/303.14 |
| 3,875,945 | 4/1975 | Friedman . |

(List continued on next page.)

FOREIGN PATENT DOCUMENTS

| | | | |
|---|---|---|---|
| 0210125 | 7/1986 | European Pat. Off. | ........ A61B 17/39 |
| 0316469 | 11/1987 | European Pat. Off. | ........ A61B 17/39 |
| 0341446 | 4/1989 | European Pat. Off. | ........ A61B 17/39 |
| 2536924 | 6/1984 | France | ........... H03K 21/36 |
| 2647683 | 7/1990 | France | ............. A61N 1/06 |
| 854366 | 8/1981 | U.S.S.R. . | |
| 2066104 | 7/1981 | United Kingdom | ........... B32B 5/14 |
| 2037167 | 7/1981 | United Kingdom | ........... A61B 17/36 |
| 2161082 | 8/1986 | United Kingdom | ........... A61B 17/36 |
| 2213381 | 8/1989 | United Kingdom | ........... A61B 17/39 |

OTHER PUBLICATIONS

"Electrosurgical Units", Evaluation, *Health Devices*, Sep.–Oct. 1987, pp. 291–342.

*Bovie 400 SR Electrosurgical Unit*, 3 page product description, Clinical Technology, Division of Sybron Corporation, date circa 1987.

*Model 9600 and Model 9601 Electrosurgery Generator, Specification and Features*, 1 page product specification, Concept Electrosurgical Products, date circa 1987.

*Model 774 Electrosurgical Generator*, 1 page product specification, The Birtcher Corporation, date circa 1987.

*Neomed Omega Electrosurgical Generator*, 2 page product description, Neomed, Inc., date circa 1987.

*Valleylab SSE2L Isolated Electrosurgical Generator*, 2 page product description, Valleylab, Inc., date circa 1987.

*Valleylab Force 2 Electorsurgical Generator*, 1 page product description, Valleylab, Inc., date circa 1987.

*The Bovie X–10 Electrosurgical Unit*, 1 page product description, Clinical Technology, date circa 1987.

(List continued on next page.)

Primary Examiner—Randall L. Green
Assistant Examiner—P. Zuttarelli
Attorney, Agent, or Firm—Fish & Neave; Nicola A. Pisano

[57] ABSTRACT

Methods and apparatus are provided for use in performing electrosurgery, wherein a power supply supplies an electrosurgical instrument with a low voltage power signal having a substantially constant peak-to-peak voltage that is independent of the load impedance and which has a crest factor near unity. A power supply is provided to supply a voltage waveform in accordance with the methods of the invention. A clipping circuit is also provided to permit practice of the methods using conventional electrosurgcial generators and previously known electrosurgical instruments, wherein the voltage amplitude and waveform is modified to the desired regime.

14 Claims, 10 Drawing Sheets

U.S. PATENT DOCUMENTS

| | | | |
|---|---|---|---|
| 3,980,085 | 9/1976 | Ikuno | 128/303.17 |
| 4,005,714 | 2/1977 | Hiltebrandt | 128/303.17 |
| 4,030,501 | 6/1977 | Archibald . | |
| 4,041,952 | 8/1977 | Morrison, Jr. et al. | 606/42 |
| 4,054,143 | 10/1977 | Bauer | 128/303.17 |
| 4,092,986 | 6/1978 | Schneiderman | 128/303.14 |
| 4,154,240 | 5/1979 | Ikuno et al. | 128/303.14 |
| 4,196,734 | 4/1980 | Harris . | |
| 4,232,676 | 11/1980 | Herczog | 606/50 |
| 4,338,940 | 7/1982 | Ikuno | 128/303.14 |
| 4,370,980 | 2/1983 | Lottick | 128/303.17 |
| 4,492,231 | 1/1985 | Auth | 606/40 |
| 4,590,934 | 5/1986 | Malis et al. | 128/303.14 |
| 4,651,734 | 3/1987 | Doss et al. | 128/303.14 |
| 4,657,016 | 4/1987 | Garito et al. | 128/303.13 |
| 4,658,819 | 4/1987 | Harris et al. . | |
| 4,685,459 | 8/1987 | Koch et al. | 128/303.17 |
| 4,752,864 | 6/1988 | Clappier | 363/86 |
| 4,862,890 | 9/1989 | Stasz et al. | 128/303.14 |
| 4,903,696 | 2/1990 | Stasz et al. | 606/37 |
| 4,938,761 | 7/1990 | Ensslin | 606/31 |
| 4,958,539 | 9/1990 | Stasz et al. | 76/104.1 |
| 4,961,739 | 10/1990 | Thompson | 606/37 |
| 4,969,885 | 11/1990 | Farin | 606/38 |

OTHER PUBLICATIONS

*Power Units, Accessories, Aspen MF380, MF360B, MF180, MF180A Electrosurgical Units,* 2 page product description, Aspen Labs, Inc., date circa 1987.

*Micro 180 Specifications,* 2 page product description, Aspen Labs, Inc., date circa 1987.

*Specification Summary, Aspen MF360A,* 1 page product description, Aspen Labs, Inc., date circa 1987.

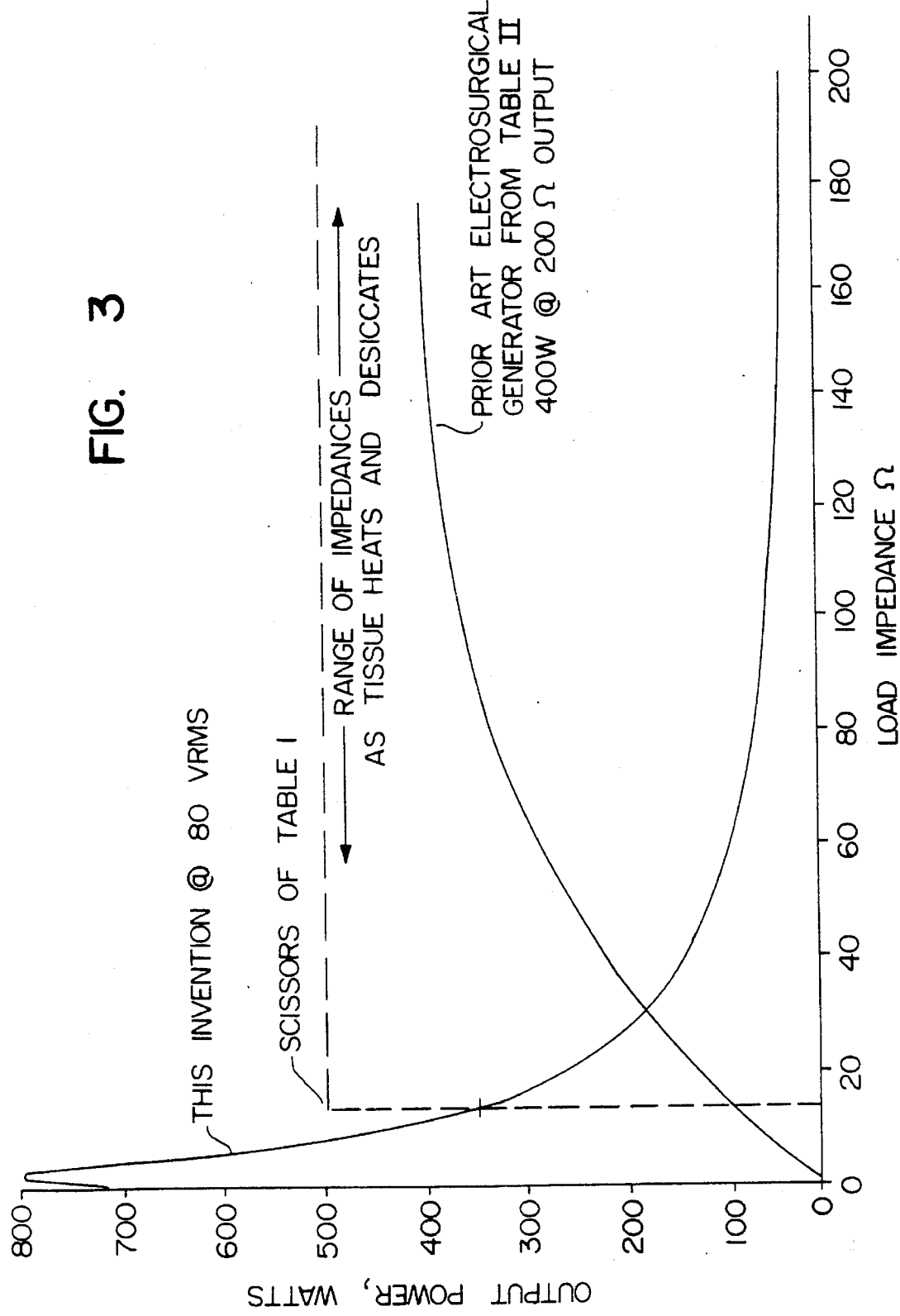

ELECTROSURGICAL APPARATUS EMPLOYING CONSTANT VOLTAGE AND METHODS OF USE

This is a continuation of application Ser. No. 07/877,533, filed May 1, 1992, entitled ELECTROSURGICAL APPARATUS EMPLOYING CONSTANT VOLTAGE AND METHODS OF USE, now abandoned, which is a CIP of application Ser. No. 07/711,920, filed Jun. 7, 1991, now abandoned.

This invention relates to the use of hemostatic electrosurgical instruments in conjunction with a power supply having a voltage output waveform effective in reducing coagulum buildup on hemostatic electrosurgical instruments.

BACKGROUND OF THE INVENTION

The control of bleeding during surgery accounts for a major portion of the time involved in an operation. In particular, bleeding that occurs when tissue is incised or severed can obscure the surgeon's vision, prolong the operation, and adversely effect the precision of cutting. Blood loss from surgical cutting may require blood infusion, thereby increasing the risk of harm to the patient.

Hemostatic electrosurgical techniques are known for reducing bleeding from incised tissue prior to, during, and subsequent to incision. Bipolar electrosurgical techniques generally pass a high voltage-high frequency current through the patient's tissue between two electrodes for both cutting and coagulating tissue. This current causes joulean (ohmic) heating of the tissue as a function of the current density and the resistance of the tissue. The heat deposited in the tissue therefore coagulates the blood in the vessels contained in the tissue, thereby reducing the blood flow from severed vessels and capillaries.

Previously known electrosurgical instruments have generally conducted current to the patient's tissue in the form of a high voltage electric arc. For cutting tissue, the current magnitude and waveform may be selected so that the current arc causes evaporation of bodily fluids at a rate sufficient to sever the tissue. For causing hemostasis, the current arc provides a generally lower energy deposition rate that desiccates tissue to stem bleeding when the tissue is incised.

A drawback encountered with many previously known electrosurgical devices is that of controlling the current flow through the patient's tissue to obtain hemostasis in localized areas without also heating and causing undesirable trauma to adjacent tissue. Difficulty in predicting the depth of penetration of the electric arc creates uncertainty concerning precisely which tissue areas are being effected. Thus, for example, the electric arc may deposit insufficient energy to cause hemostasis at one site, while due to preferential resistance of the tissue, an electric arc of similar energy may lead to deep tissue necrosis if conducted to an adjacent tissue site.

Another drawback of previously known electrosurgical devices is the tendency of the current arc to promote charring of the tissue. In electrosurgical devices, the current arc and the patient's tissue form series components of an electrical circuit. The product of the voltage and the current represents the power loss attributable to each of these components. For previously known electrosurgical devices, the power dissipation in the current arc may exceed that in the patient's tissue. Consequently, the electric arc or flame generated by the electrosurgical device typically has very high temperatures, on the order of thousands of degrees. This electric flame can surround the tissue adjacent to the working surface of the device, and quickly lead to desiccation and charring of the tissue. While the electric flame thus cuts and causes hemostasis of the patient's tissue, it frequently results in charring of the tissue, which inhibits rapid regrowth of the tissue.

Yet another drawback of previously known electrosurgical devices, due in part to the wide variation in peak-to-peak voltage inducing the electric arc, is a tendency of the coagulated blood or severed tissue to adhere to the working surfaces of the instrument. This buildup, referred to as "coagulum," increases the electrical resistance of the path along which current flowing between the electrodes of the electrosurgical instrument must travel. A consequence of coagulum buildup on the instrument during an operation is that the electrical energy deposited in the tissue being heated or severed decreases, until the current flowing through the tissue is no longer sufficient to cause adequate cutting or hemostasis.

Consequently, the surgeon must frequently pause during surgery to scrape coagulum off of the working surfaces of the electrosurgical instrument. This scraping step increases the time and labor expended by the surgeon that is not directed to attaining the goal of the operation. Furthermore, inasmuch as this step of scraping the working surfaces of the instrument is not undertaken until there is inadequate hemostasis, there is additional blood loss from the severed tissue while the coagulum is scraped off the instrument.

A yet further drawback of previously known electrosurgical instruments is a tendency of tissue to adhere to the coagulum on the instrument. This sticking of tissue to the instrument can result in tearing of previously congealed tissue, thereby reactivating blood flow from that tissue. Additionally, such sticking of the instrument to previously congealed tissue can limit maneuverability of the instrument at the surgical site, thereby increasing the physical effort required by the surgeon to move the instrument about to accomplish the goal of the operation. Finally, such sticking, and the increased probability of reactivating blood flow by tearing previously coagulated tissue, can reduce the surgeon's field of vision of the working tip of the instrument and reduce the precision of the cutting.

Previously known electrosurgical instruments have employed generators generally providing alternating-current (AC) voltages in the range of 150 to 5000 volts peak-to-peak at power ratings of less than 400 watts. Such generators typically operate with current frequencies in the range above 100 kHz, because frequencies below 100 kHz are known to cause undesirable neuromuscular stimulation in the patient. It is also typical of previously known electrosurgical generators to provide power output to instruments rated between 100 and 400 ohms. To provide impedance matching of the power supply with the electrosurgical instruments, such power supplies also have high output impedance.

Malis et al. U.S. Pat. No. 4,590,934 describes an electrosurgical generator for use with a bipolar cutter/coagulator. The generator described in that patent generates a power output waveform comprising groups of aperiodic sequences of damped bursts of high frequency signals. The generator damps the high initial voltage spike at the onset of the electric arc generated by the electrosurgical device, to reduce sparking at the instrument tips and the undesirable equipment interference created by the initial spark of the electric arc.

Schneiderman U.S. Pat. No. 4,092,986 and Farin U.S. Pat.

No. 4,969,885 describe generators for use with electrosurgical instruments whereby the output voltage of the generator is maintained at a substantially constant level, independent of the impedance encountered by the electrosurgical instrument Schneiderman U.S. Pat. No. 4,092,986 describes the use of an unmodulated RF voltage waveform for cutting tissue and a pulse modulated RF voltage waveform for coagulating tissue. The patent teaches use of voltages in the range of 450 to 600 volts peak-to-peak with currents in the range of approximately zero to 0.6 amperes peak-to-peak.

Farin U.S. Pat. No. 4,969,885 notes that a minimum effective voltage of at least 150 volts (RMS) (420 volts peak-to-peak) is required for use in electrosurgical cutting instruments, in order to provide the electric field strength necessary to ignite and maintain electric arcs between the electrode and the tissue. That patent also notes that to provide constant voltage to the electrosurgical device throughout the anticipated range of operating conditions, it is desirable that the high frequency voltage generator provide a waveform that is independent of the operating conditions, and preferably a pure sine wave.

Electrosurgical instruments operated with voltages above 150 VRMS, and relatively low currents are believed to experience the coagulum buildup and associated problems described heretofore. These difficulties with coagulum buildup have limited the growth of the field of electrosurgery.

Herczog U.S. Pat. No. 4,232,676 describes an electrosurgical scalpel and method of use of that scalpel that attempts to overcome the drawbacks of coagulum buildup and charring associated with the use of high voltage electric arcs. That patent describes the use of low voltages, in the range of 20 to 80 volts, that prevent arcing and result in energy deposition rates of 5 to 50 watts. The scalpel described in that patent has heretofore achieved only limited commercial success, due in large part to the teaching of that patent that power be regulated by varying the frequency of the supplied voltage waveform.

It would therefore be desirable to provide an electrosurgical system that overcomes the problems of coagulum buildup and sticking that have plagued previously known electrosurgical devices and limited application of electrosurgery in surgical procedures.

It would be desirable to provide an electrosurgical generator capable of supplying low voltages at high power. Such a power supply would reduce arcing at the electrode, and the charring of tissue and sticking that typically accompany such arcing.

It would furthermore be desirable to provide an electrosurgical generator having a low output impedance that supplies a substantially constant voltage output level that is independent of the load impedance. Such a power supply would therefore maintain voltage at a preselected level, and thus avoid excessive energy deposition as tissue impedance increases during hemostasis.

In view of the limited room available in an operating room, and the size limitations imposed by heat dissipation requirements, it would also be desirable to provide an efficient and compact electrosurgical power supply.

SUMMARY OF THE INVENTION

In view of the foregoing, it is an object of this invention to provide an electrosurgical system, and methods of the use of that system, that overcome the problems of coagulum buildup and sticking that have hampered the use of previously known electrosurgical devices.

It is an object of the present invention to provide apparatus and methods for supplying lower voltages than typical of previously known devices, and at high power. The power supplies constructed in accordance with the principles of the present invention prevent arcing at the instrument electrodes, and thus the charring of tissue and sticking that typically accompany such arcing.

It is another object of the present invention to provide electrosurgical generators having low output impedance that supply a substantially constant voltage output level that is independent of the load impedance. The low output impedance of the power supply of the present invention reduces the likelihood of voltage excursions when the tissue impedance increases during the desiccation process.

These and other objects are accomplished in accordance with the principles of the present invention by providing alternating-current (AC) power supplies having an output impedance of less than 20 ohms that are capable of providing a substantially constant output voltage level. The power supplies of the present invention operate in a regime of 10–130 volts (RMS) and currents up to 7 amperes, thereby providing energy deposition rates at the electrodes of connected electrosurgical instruments in the range of 50–700 watts, depending upon the type of electrosurgical instrument in use and the type of tissue being operated upon.

To substantially reduce arcing at the instrument electrodes, while improving voltage regulation and power delivery, the power supplies of the present invention provide a waveform having a crest factor near unity. Applicants have determined that the application of low crest factor waveforms reduce the peak-to-peak voltage swing in the tissue, while providing greater rates of power deposition. The voltage waveforms supplied by these power supplies result in improved hemostasis of the tissue, but without the charring observed with previously known electrosurgical apparatus. A power supply constructed in accordance with the present invention includes a modulator with an adjustable duty-cycle that allows the selection of the output voltage level. A selectable voltage produced by the modulator is received by an inverter, which transforms this voltage and supplies the transformed voltage to the surgical instruments in response to a low power constant voltage square wave that is also an input to the inverter. The modulator circuitry accepts a control signal that varies the duty-cycle of a portion of the circuitry that self-oscillates. A stable adjustable output voltage is provided by averaging these oscillations.

In an alternative embodiment of the present invention, retrofit devices are provided for use with a variety of previously known electrosurgical generators, whereby the output of those generators is converted to the regime of voltage and current contemplated by the present invention. Illustrative retrofit devices are described for use with a number of previously known electrosurgical generators, so that these devices may be used in accordance with the methods of the present invention.

The present invention includes methods of supplying power to electrosurgical instruments to cause hemostasis in tissue without the coagulum buildup and sticking problems encountered with prior art devices. In accordance with the present invention, electrosurgery is performed using instruments having electrodes for depositing heat in tissue without arcing, thereby desiccating and weakening the tissue when it is desired to cut tissue, as well as cause hemostasis. Mechanically sharp edges are provided on the instruments to then sever the desiccated tissue. The methods include the steps of:

(a) providing a surgical instrument having an electrode;

(b) connecting the electrode to an AC power supply;

(c) selecting and maintaining a substantially constant output voltage level that is independent of the load impedance, wherein the alternating current (AC) voltage waveform has a crest factor near unity; and (d) placing the electrode in electrical contact with tissue so that high frequency current passes through the tissue, without arcing, to partially desiccate the tissue to cause hemostasis.

Where it is desired to sever the tissue, in addition to causing hemostasis, the methods further comprise the steps of providing a mechanically sharp edge on the surgical instrument and manipulating the surgical instrument so that the mechanically sharp edge severs the partially desiccated tissue.

BRIEF DESCRIPTION OF THE DRAWINGS

The above and other objects and advantages of the invention will be apparent upon consideration of the following detailed description, taken in conjunction with the accompanying drawings, in which like reference numerals refer to like parts throughout, and in which:

FIG. 3 shows a comparison of the electrical output characteristics of an illustrative power supply of the present invention to a typical previously known power supply;

DETAILED DESCRIPTION OF THE INVENTION

Figure 1:
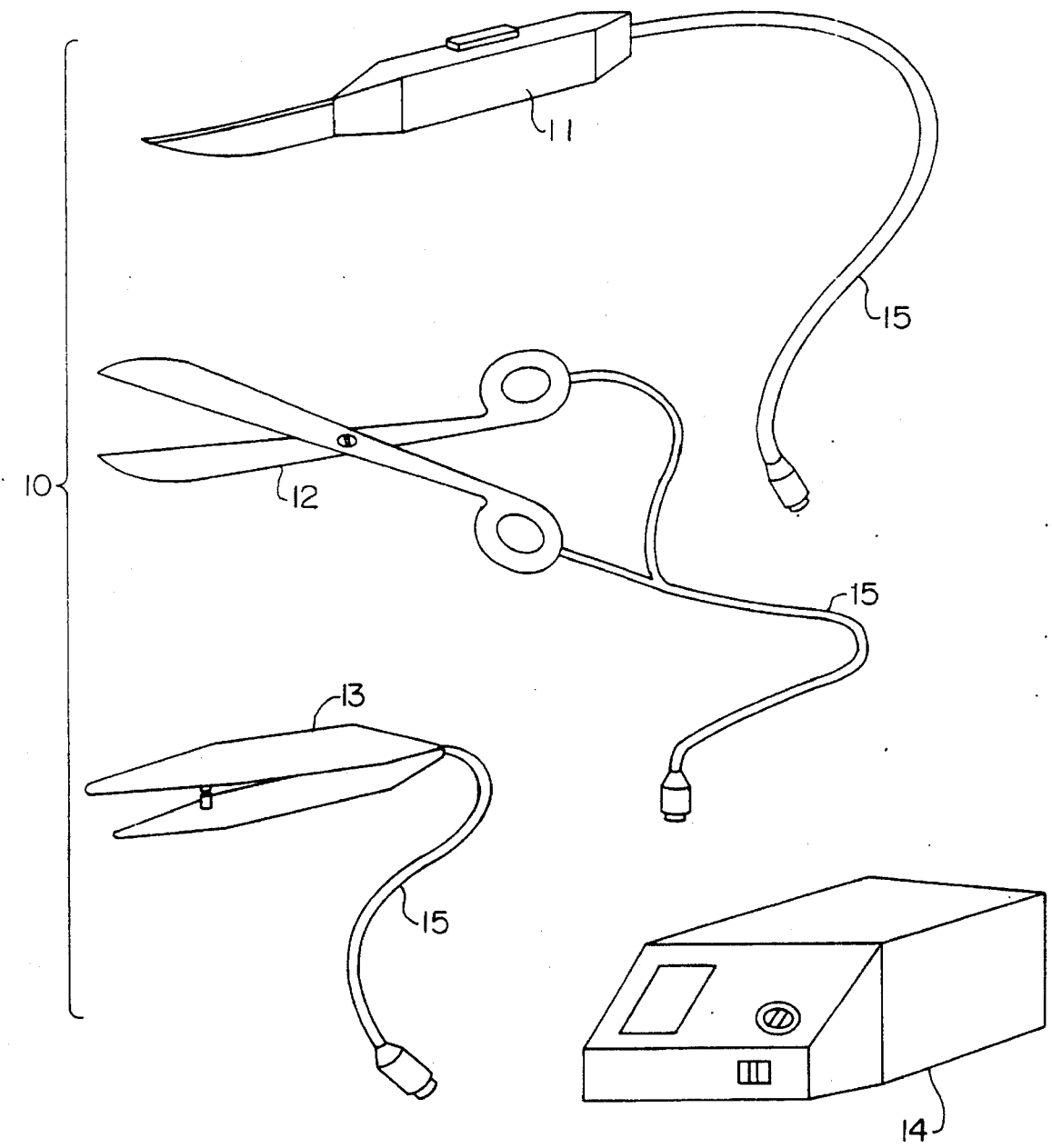
FIG. 1 is an elevated perspective view of an illustrative electrosurgical apparatus constructed in accordance with the present invention.

Referring to FIG. 1, electrosurgical apparatus 10 of the present invention is described. Apparatus 10 comprises one of a plurality of electrosurgical instruments, such as scalpel 11, scissors 12, or graspers 13, in combination with a power supply 14 constructed in accordance with principles of the present invention. The scalpel may be that described in Herczog, U.S. Pat. No. 4,232,676, while the scissors may be constructed as described in U.S. patent application Ser. No. 07/877,703, filed May 1, 1992 or U.S. patent application Ser. No. 07/877,704, filed May 1, 1992. Each of instruments 11, 12, and 13 includes a cable 15 by which the instruments are connected to power supply 14. Each instrument preferably comprises a pair of bipolar electrodes to cause hemostasis. A mechanically sharp cutting edge is also provided, if it is desired to cut tissue. In accordance with the present invention, power supply 14 supplies a substantially constant voltage alternating-current (AC) waveform to the connected electrosurgical instrument, wherein the waveform has a crest factor near unity and the voltage is in the range of 10–130 volts RMS.

Applicants have determined that the elimination of arcing and the use of low voltage, low crest factor waveforms at high power provides improved performance of known electrosurgical devices relative to previously known methods of employing such instruments. The method of the present invention has furthermore lead to the development of novel electrosurgical instruments that exploit the advantages provided by such methods.

Two principle drawbacks of previously known electrosurgical devices are coagulum buildup on the working surface of the instrument and sticking of tissue to the working surface of the device. Applicants have determined that both of these problems result from the teaching of previously known devices that it is desirable to use high voltage, low current, voltage waveforms having large crest factors to produce electric arcing at the instrument electrodes. For example, Farin, U.S. Pat. No. 4,969,885, notes that 150 volts RMS is required to achieve electrical arcing for hemostatically cutting tissue. The solution to the problem of coagulum buildup and sticking, as determined by the applicants, is to move away from the high voltage and low power/cycle typical of previously known devices, and toward the use of lower voltage, higher power/cycle waveforms having a crest factor near unity. Instead of using a current arc to cut tissue, the present invention relies on the use of current passing through tissue to heat and desiccate the tissue, thereby facilitating bloodlessly cutting the tissue with a mechanically sharp edge.

Figure 2:
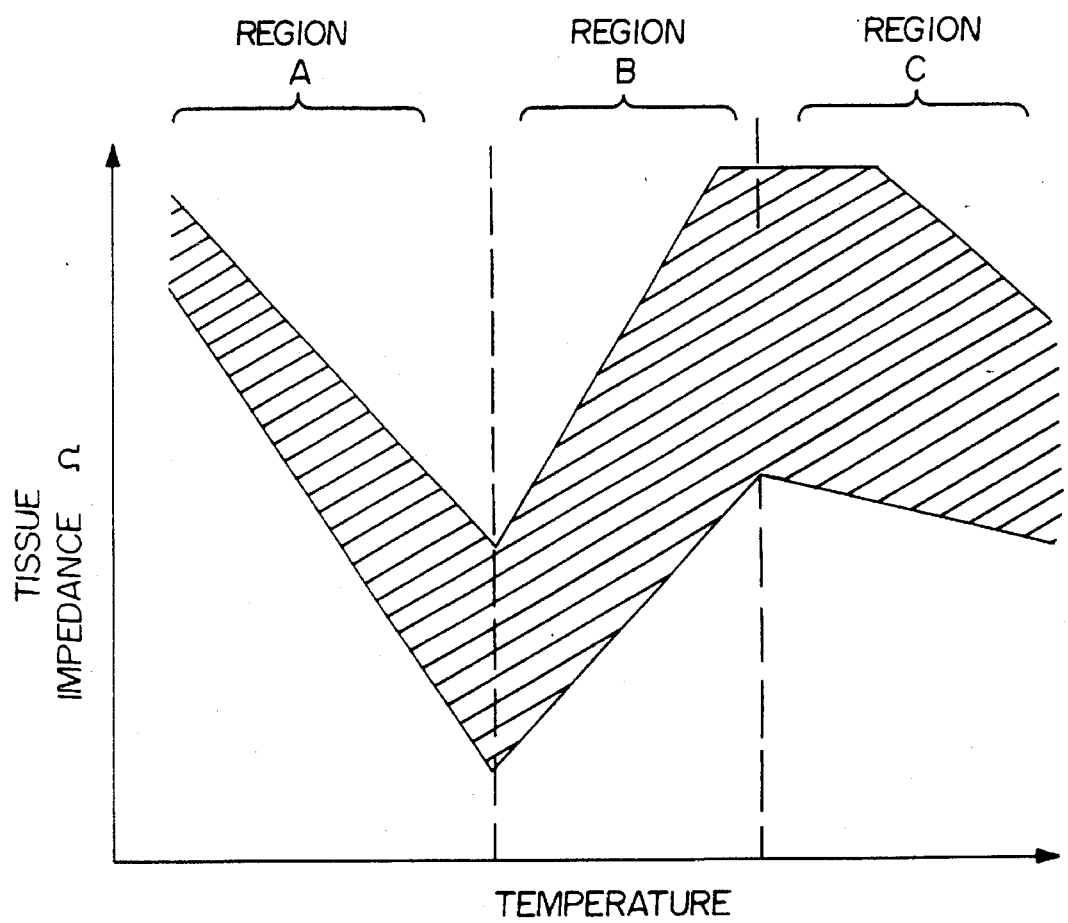
FIGS. 2 is a schematic diagram of tissue impedance versus temperature observed from applicants' research.

Referring to FIG. 2, a schematic diagram showing the variation of impedance to current flow versus temperature for typical body tissue, as observed from applicants' research, is described. Body fluids, such as those surrounding and contained within tissue, comprise primarily water and various salts. When heat is applied to tissue, the salts contained within the body fluids are believed to dissociate, thereby decreasing the electrical impedance of the tissue (region A). As the water warms it expands, causing cell walls to rupture, thus removing these barriers to ion movement and further reducing the tissue impedance. Continued heating of the tissue causes the evolution of steam, which at first improves conduction by rupturing cell walls, but then causes the impedance to increase as the water boils away, leading to desiccation of the tissue (region B). Once the water has boiled way, further heating of the tissue causes it to carbonize, or char, resulting in some decrease in impedance.

Applicants have determined from their research that useful hemostasis and hemostatic cutting can be achieved by operating electrosurgical instruments in regions A and B of FIG. 2. In these regions, the application of a substantially constant voltage first leads to increasing currents, as the tissue warms, and then to desiccation of the tissue, as a portion of the cell fluids boil away.

Operation of an electrosurgical instrument in regime B is especially useful for severing the tissue with a mechanically sharp edge, since the evolving steam serves to weaken the tissue by rupturing the cell walls of the cells comprising the tissue. Furthermore, operation of the electrosurgical instrument in this regime provides a self-limiting action. For a substantially constant voltage input, the increasing impedance of the desiccating tissue reduces the current, so that, depending upon the voltage level, the tissue temperature achieves a thermal equilibrium at a temperature below that at which charring occurs.

Previously known electrosurgical devices operate mostly in region C of FIG. 2, and employ waveforms having high peak-to-peak voltages that generate an electric arc for causing hemostasis and cutting tissue. The electric arc is typically associated with temperatures of thousands of degrees—such that it causes the tissue receiving the arc to quickly pass through regions A and B, leading to charring in region C. Consequently, the almost instantaneous desiccation caused by such devices make the tissue more likely to stick to the instrument.

Applicants have determined that even when electric arcing is not observed, for example, at relatively low voltages, wide fluctuations in the applied peak-to-peak voltage can result in undesirable sticking and coagulum buildup. Accordingly, applicants have determined that the use of voltage waveforms having a ratio of peak voltage to root-mean-square (RMS) voltage—"crest factor"—near unity reduces the tendency of voltage fluctuations to cause coagulum buildup. For example, a square wave has a crest factor of one, while a pure sine wave has a crest factor 1.41. A square wave having a peak voltage of less than 130 volts RMS has been observed by the applicants to provide good hemostasis, without noticeable sticking or coagulum buildup.

Research conducted by the applicants has determined that the amount of sticking and coagulum buildup is directly related to the peak-to-peak voltage applied to the electrosurgical instrument—the higher the peak-to-peak voltage, the faster and more tenacious the coagulum buildup. Moreover, for a given peak voltage, the greater the crest factor of the voltage waveform, the faster the coagulum buildup. In a study employing 7-inch bipolar electrosurgical scissors constructed as described in copending, commonly assigned U.S. patent application Ser. No. 07/877,703, filed May 1, 1992 the applicants obtained the results shown in Table I for fresh beefsteak as a function of the voltage level and waveform.

TABLE I

| Voltage Level (RMS) | (peak-to-peak) | Waveform | Crest Factor | Number of Cuts |
|---|---|---|---|---|
| 80 | 160 | square | 1.0 | >50* |
| 120 | 336 | sine | 1.41 | 8 |
| 140 | 392 | sine | 1.41 | 2 to 3 |

"Number of Cuts" is that number of cuts that could be made in the tissue before the delivered current decreased by 85%, i.e., to the point where the electrodes were so coated with coagulum that they would no longer provide effective hemostasis. Applicants determined that for a square wave voltage signal of 80 volts RMS, 50 cuts could be made in the tissue with no measurable decrease in the measured current. In other similar tests, applicants have observed that the use of an 85 volt RMS ("VRMS") square wave yields highly satisfactory hemostasis, whereas an 85 VRMS sine wave (119 volts peak) causes sticking and only limited hemostasis.

The methods and apparatus of the present invention are particularly well-suited for use with the electrosurgical scalpel described in Herczog, U.S. Pat. No. 4,232,676. Although that patent describes the use of low voltages such that no arcing is produced, the device described therein has not achieved commercial success, because it too was subject to coagulum buildup and sticking. Use of instrument constructed in accordance with that patent, and operated with the voltage, current and waveform regimes of the present invention, is expected to provide highly satisfactory results. Applicants believe that it is the lack of appreciation of the importance of the crest factor, as well as the power supply output impedance characteristics described hereinafter, that accounts for the success that can now be achieved with the Herczog instruments.

Referring again to FIG. 2, another aspect of the importance of the crest factor is described. Applicants have observed that to promote effective hemostasis with a device having a mechanically sharp cutting edge, it is desirable to rapidly heat the tissue through region A. For a power supply having a peak output voltage of 100 volts, a square wave applies the full 100 volts to the tissue, while a sine wave effectively applies only 71 volts during the same time period. Because the heat deposited in the tissue is approximately $V^2/R$, application of the square wave provides, on average, twice the power of a sine wave, assuming constant tissue impedance. Consequently, the square wave more quickly heats the tissue, so that the surgical instrument can provide instantaneous hemostatic action and cutting.

Referring now to FIG. 3, another aspect of the present invention is to provide substantially constant voltage to the electrosurgical instrument using a power supply having an output impedance of only a few ohms, generally 20 ohms or less. When the output impedance of the power supply is less than that of the tissue, the voltage output by the power supply neither falls when loaded, nor rises excessively in response to increased load impedance. Rather, power delivery to the tissue is primarily a function of the user-selected output voltage and the resistance of the tissue, according to $V^2/R$, and not of source-to-load impedance match. Electrosurgical instruments suitable for use with the methods and power supply of the present invention also have relatively low impedances. For example, the 7-inch scissors employed to obtain the data shown in Table I have an impedance of about 16 ohms.

Previously known electrosurgical generators are typically designed for delivering power to an instrument having an impedance in the range of 100–400 ohms. Such conventional power supplies typically have an output impedance of 200 ohms or more, and poorly regulated voltages. Referring to FIG. 2 in conjunction with FIG. 3, it is observed that as the impedance of the tissue rises during desiccation (region C), the output voltage of a typical power supply also rises because of the large output impedance associated with such power supplies. This rise in output voltage results in increased power delivery to the tissue, thereby accelerating the depth and extent of charring. Such behavior further promotes sticking, coagulum buildup, and tissue necrosis, problems that are substantially reduced with power supplies constructed in accordance with the present invention. Power characteristics for some previously known electrosurgical generators are shown in Table II, as obtained from product literature of those generators or *Health Devices*, September–October 1987, "Waveform Measurement Results", page 310–311, published by ECRI, Plymouth Meeting, Pa.

TABLE II

| Maker | Model No. | Wave-form | Output[1] Impedance | Pk-to-Pk Voltage[2] | Max.[3] Power |
|---|---|---|---|---|---|
| This invention | | square | ~5 | 200 | 500 |
| Aspen | MF180 | sine | 300 | 1800 | 50 |
| | MF360B | sine | 200 | 2300 | 70 |
| | MF380 | sine | 100 | 2000 | 55 |
| Bard | Sys 5000 | sine | 125 | 1800 | 45 |
| Clinical Tech. | X-10 | sine | 100 | 1500 | 70 |
| Concept | 9900 | sine | 200 | 1950 | 49 |
| Elmed | 170 M/M | sine | 100 | 1750 | 61 |
| | 300 M/M | sine | 100 | 2100 | 60 |
| Bovie | 400-SR | sine | 400 | 4000 | 50 |
| Birtcher | 774 | sine | 300 | 1000 | 22 |
| Neomed | 3000 | sine | 100 | 1800 | 50 |
| | Omega | sine | 100 | 2000 | 49 |
| Valleylab | SSE2L | sine | 100 | 2300 | 90 |
| | Force 2 | sine | 100 | 1700 | 70 |
| | Force 4 | sine | 100 | 1500 | 70 |

[1] Output Impedance at peak power output, in ohms.
[2] Pk-to-Pk voltage is the maximum open circuit peak-to-peak voltage in volts, in monopolar cut mode.
[3] Max. Power is the maximum power output in bipolar cut mode, in watts.

While Table II is not intended to be all-inclusive, it is generally representative of the performance characteristics of previously known electrosurgical generators. Of particular interest are the voltage waveforms, high open-circuit voltages, high output impedances and low power outputs of these devices compared to the power supply of the present invention.

From Table II, it is observed that none of the listed electrosurgical generators provides other than a sinusoidal waveform. Furthermore, each of these previously known generators provides high peak-to-peak output voltage levels at output impedances that tend to lead to charring of tissue.

The methods of the present invention include supplying AC power to electrosurgical instruments to cause hemostasis in tissue without the coagulum buildup and sticking problems encountered with prior art devices. In accordance with the present invention, electrosurgery is performed using instruments having electrodes for passing high frequency current to tissue without arcing, thereby desiccating and weakening the tissue when it is desired to cause hemostasis. When it also desired to cut tissue, mechanically sharp edges are provided on the instruments to sever the desiccated tissue. The methods include the steps of:

(a) providing a surgical instrument having an electrode;

(b) connecting the electrode to an AC power supply;

(c) selecting and maintaining a substantially constant output voltage level that is independent of the load impedance, wherein the alternating-current (AC) voltage waveform has a crest factor near unity;

(d) placing the electrode in electrical contact with tissue so that AC current passes through the tissue, without arcing, to partially desiccate the tissue to cause hemostasis.

When it is desired to sever tissue, as well as cause hemostasis, the methods further comprise the steps of providing a mechanically sharp edge on the surgical instrument to sever the partially desiccated tissue. Importantly, the use of the low crest factor voltage waveform of applicants' invention permits high power deposition rates in the tissue per waveform cycle, so that the blood vessels in the tissue may be coagulated simultaneously with cutting of the tissue.

Applicants have determined that for the 7-inch scissors referred to above with respect to Table I, and depending upon the vascularity of the tissue being cut, current levels up to 7 amperes (providing up to 700W of power) may be applied to achieve simultaneous hemostasis and cutting, and with little coagulum buildup.

Applicants' method further includes the steps of providing a power supply having a low output impedance, to provide the self-limiting voltage regulation described heretofore with respect to FIG. 3. Applicants' method of performing electrosurgery hemostatically using a low crest factor, low voltage, high power/cycle waveform is applicable to a large number of electrosurgical devices. In addition to the hemostatic instruments described in copending, concurrently filed and commonly assigned U.S. patent applications Ser. No. 07/877,703, filed May 1, 1992, and Ser. No. 07/877,704, filed May 1, 1992, and Ser. No. 07/877,538, filed May 1, 1992, applicants contemplate that their invention can be successfully applied to the electrosurgical scalped blade described in Herzog U.S. Pat. No. 4,232,676, and the bipolar forceps and graspers of FIGS. 4 and 5.

Figure 4A:
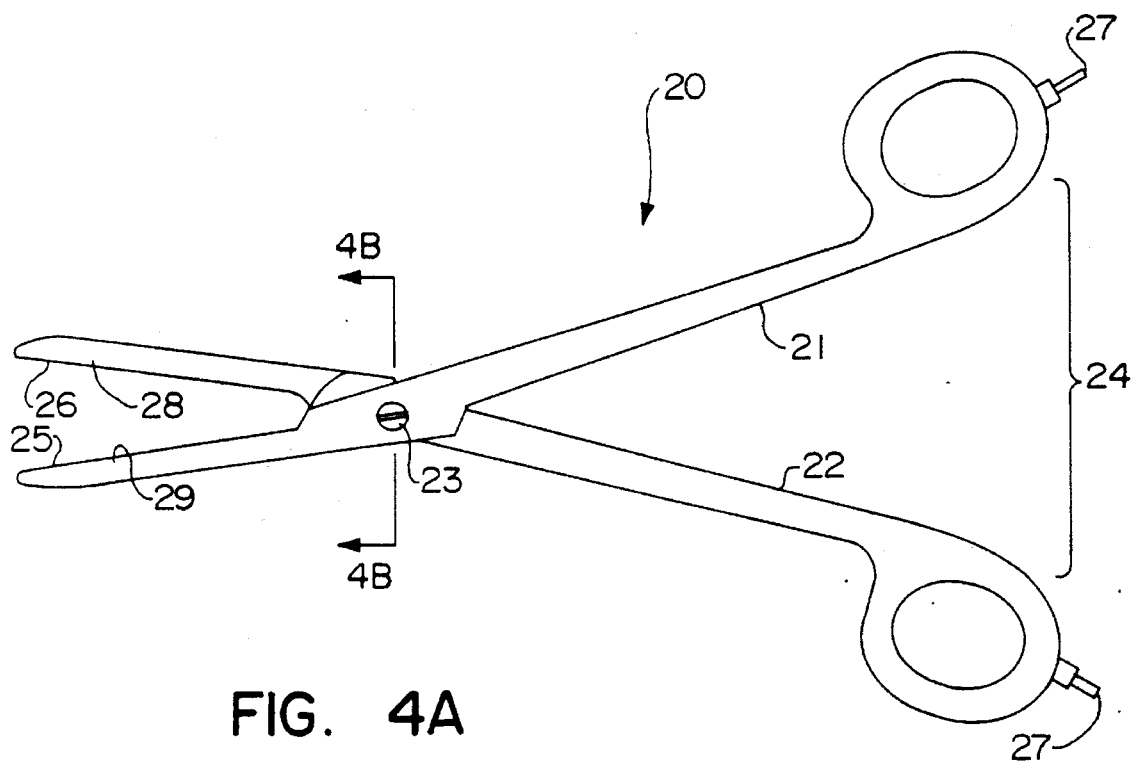
FIGS. 4A and 4B, show, respectively, side and cross-sectional views of a bipolar electrosurgical forceps suitable for use with the apparatus and methods of the present invention.
Figure 4B:
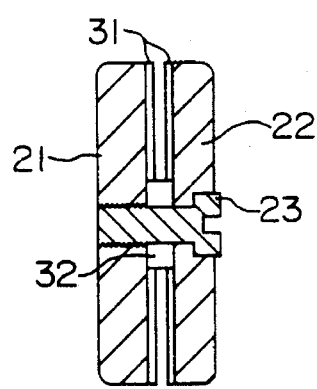

Referring to FIGS. 4A and 4B, bipolar forceps 20 suitable for use with the methods of the present invention is described. Forceps 20 includes opposing support members 21 and 22, which are pivotally connected at pivot 23. The proximal ends of support members 21 and 22 form handle 24, wherein each support member 21 and 22 provides a hole for the surgeon's thumb or finger. Support members 21 and 22 are capable of moving through a conventional forceps-like motion when actuated by handle 24, such that the distal ends 25 and 26 of the support members close together to engage tissue disposed therebetween. Each of support members 21 and 22 has a terminal 27, to energize the electrode portions 28 and 29 at the distal end of the forceps. Each of support members 21 and 22 may have an insulating coating 31, for example, alumina, disposed on its surface to prevent shorting between the support members when electrodes 28 and 29 are energized.

Pivot 23 of forceps 20 is constructed of a rigid electrically insulating material, for example, alumia, zirconia or a ceramic, and includes and electrically insulating washer 31 disposed between support numbers 21 and 22 to further prevent short circuiting. Electrodes 28 and 29 do not touch when the forceps are closed.

Figure 5:
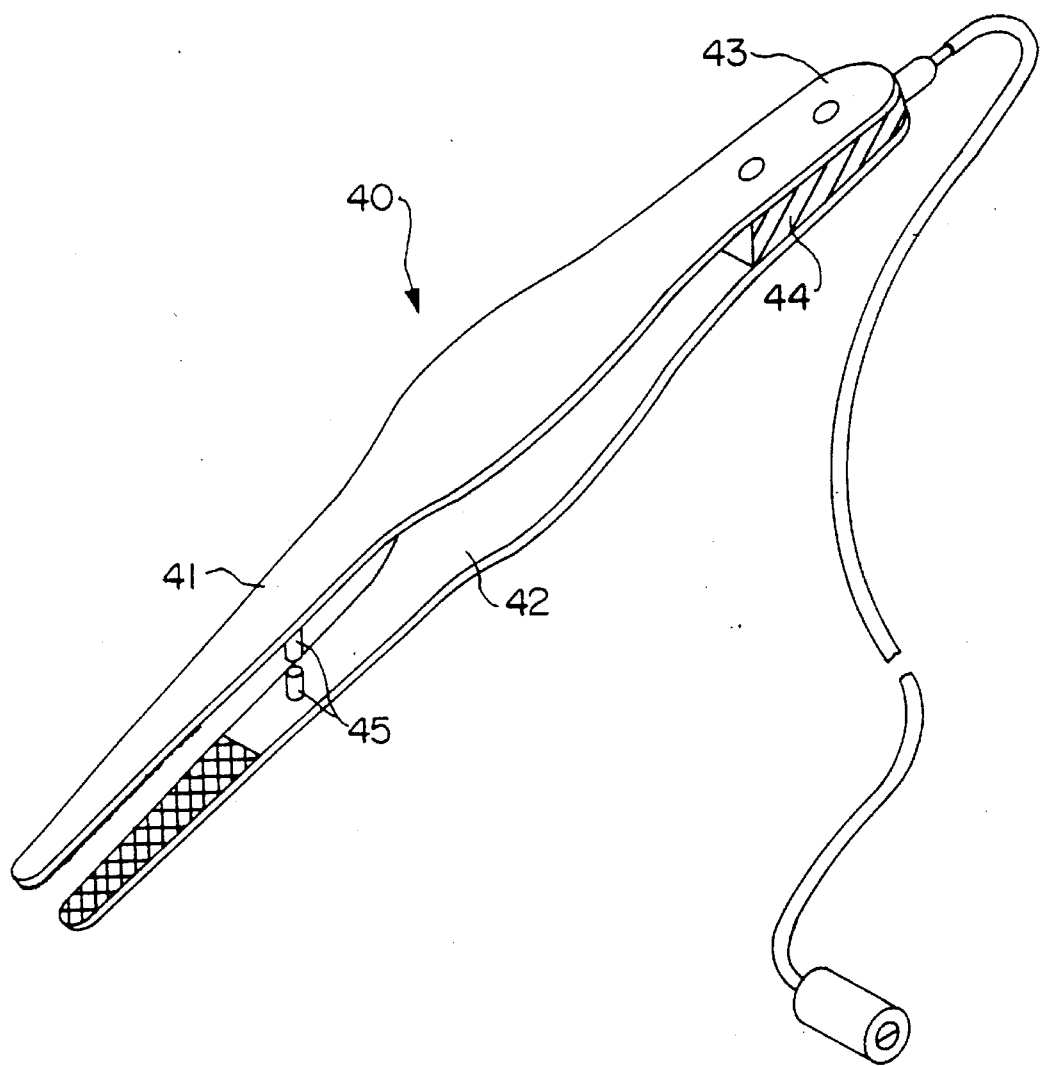
FIG. 5 shows a perspective view of a bipolar grasper suitable for use with the apparatus and methods of the present invention.

Referring to FIG. 5, hemostatic bipolar grasper 40 is described. Grasper comprises support members 41 and 42 that are joined together at junction 43 by a plate of electrically insulating material 44. Plate 44 and stops 45 comprise an electrically insulating material that serves to electrically isolate support members 41 and 42. Stops 45 are arranged to prevent the distal ends of graspers from contacting each other when the forceps are closed together. Such a grasper is described, for example, in Beurle et al., U.S. Pat. No. 3,685,518.

The method of the present invention comprises use of bipolar electrosurgical instruments as shown in FIGS. 4 and 5, and the above-noted U.S. patent application Ser. Nos. 87,703, 877,704 and 877,538, all filed on May 1, 1992, in conjunction with the power supply of the present invention. The power supply of the present invention provides low voltage, high power, low crest factor AC voltage waveforms to the instrument as described heretofore, and contains circuitry for adjusting the magnitude of the output voltage. The power supply of the present invention is also characterized by high efficiency and low power dissipation, allowing a compact configuration to be used.

Figure 6:
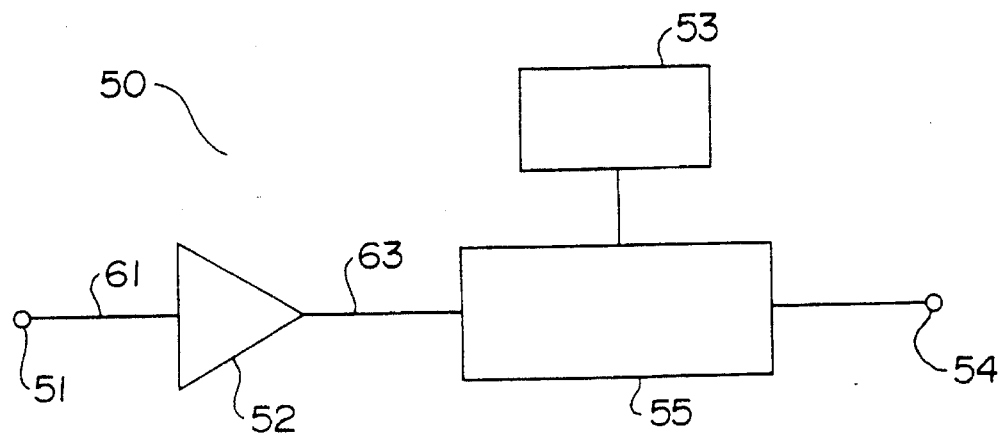
FIG. 6 is a block diagram of a preferred embodiment of a constant voltage power supply in accordance with the invention.

Referring now to FIG. 6, power supply 50 drives electrosurgical instruments via output power terminal 54. The output power signal is delivered to output terminal 54 by power inverter 55. Inverter 55 accepts a high frequency low-power AC waveform from generator 53. In accordance with principles of the present invention, this low-power AC waveform has a crest factor near unity, generally less than about 1.10, and is preferably a square wave. Generator 53 provides this driving signal at a fixed voltage and at a frequency preferably higher than 100 kHz to avoid undesirable neuromuscular stimulation in the patient. Generator 53 provides the voltage waveform, including crest factor, and frequency applied to the electrosurgical instrument, while modulator 52 and inverter 55 adjust the amplitude of the resulting waveform.

Modulator 52 provides DC voltages that may be varied from a low level to a high level. The voltage supplied by modulator 52 is determined by a control signal received via control input terminal 51. Modulator 52 employs an internal self-oscillating circuit that produces signals preferably having a frequency of oscillation in the range of 40–100 kHz. Beyond 100 kHz, the efficiency of the device decreases while below 40 kHz the generation of incidental audible noise becomes a concern. Inverter 55 delivers a voltage that is transformed from the voltage supplied by modulator 52 at a predetermined ratio. In response to the AC square wave drive signal from generator 53, inverter 55 applies the transformed drive voltage to the electrosurgical device as a square wave. Acceptable internal configurations of generator 53 and inverter 55 will be apparent to those skilled in the art and therefore the details of these components form no part of the present invention.

Figure 7:
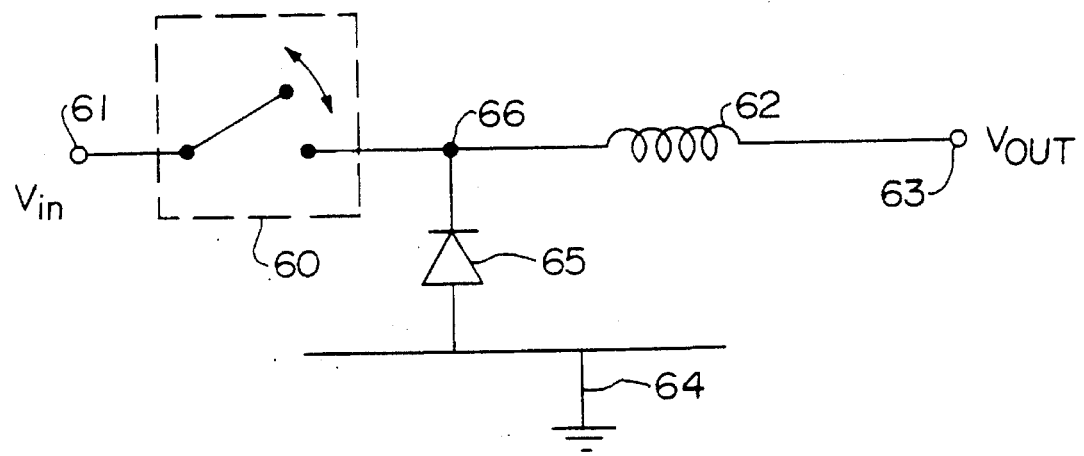
FIG. 7 is a simplified circuit diagram of a preferred embodiment of a modulator circuit for a constant voltage power supply in accordance with the invention.
Figure 8:
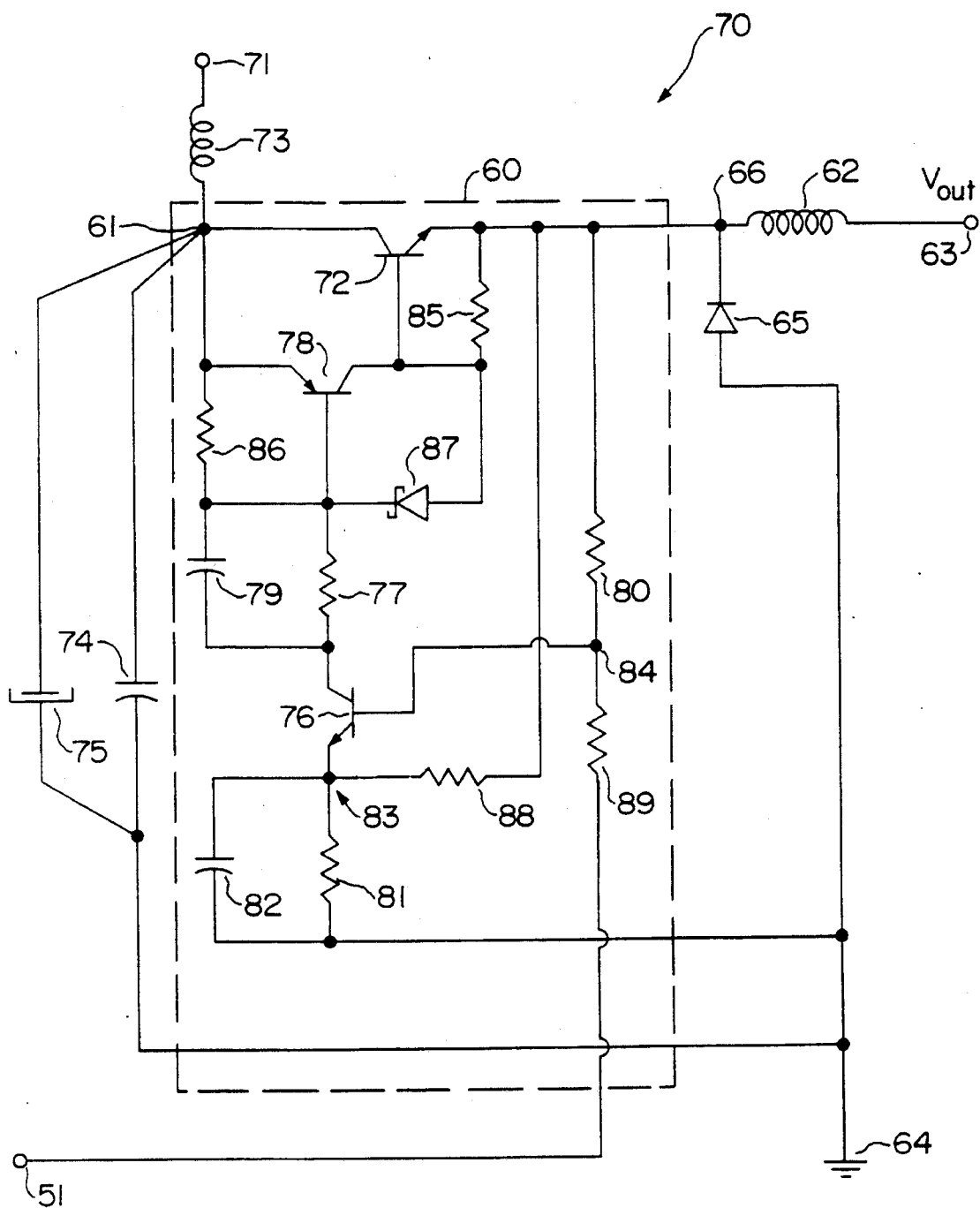
FIG. 8 is a detailed circuit diagram of a first embodiment of the modulator circuit of FIG. 7.

An embodiment of the circuitry of modulator 52 is described with respect to FIG. 7. Switch 60 is a simplified representation of the portion of the circuitry that self-oscillates. Voltage supply node 61 communicates with a power supply voltage, which may be received via terminal 71 as shown in FIG. 8. In operation, switch 60 oscillates between a conducting state and a nonconducting state with a duty-cycle that is selected based on the desired voltage level to be delivered to the instrument in use. Current passes from voltage supply node 61 via inductor 62 to modulator output 63 when switch 60 is closed. When switch 60 is opened, the current through inductor 62 into modulator output 63 is drawn from ground terminal 64 through rectifying catch diode 65. Further, when switch 60 is open the voltage at voltage supply node 61 is isolated from switch node 66. The oscillation of switch 60 thus creates a series of square pulses at node 66. Inductor 62, which may be considered an energy storage inductor, produces a well-defined DC voltage at modulator output 63 by storing energy in its magnetic field when switch 60 is closed and returning it when switch 60 is open. The voltage supplied to modulator output terminal 63 is the DC average of the square pulses at switch node 66, so that by varying the duty-cycle of switch 60, the voltage supplied to inverter 55 (see FIG. 6) may be controlled. Selection of inductor 62 need not be based on an energy storage requirement, but may be based on the current stess applied to the switch 72 and the allowable ripple voltage at modulator output terminal 63.

The circuitry of a first embodiment of modulator 52, modulator 70, is described with respect to FIG. 8. In operation, transistor 72 acts as a switch, alternately closing to provide a conducting path from voltage supply node 61 to switch node 66 and opening to interrupt this current flow. Terminal 71 is connected to a DC voltage supply, which may be a conventional DC voltage supply circuit operating at, for example, 30 VDC. Current passing through inductor 73 either flows through transistor 72 or charges capacitors 74 and 75. The charge stored on capacitors 74 and 75 provides a readily available source of current when transistor 72 turns on, thereby providing a rapid transition from low to high current at switch node 66. In combination, inductor 73 and capacitors 74 and 75 form an input filter that decouples modulator 70 from other circuitry, thereby preventing propagation of spurious frequencies in the balance of the circuit.

Oscillation of transistor 72 is driven by transistor 76. When transistor 76 is on, current flows through resistor 77 and through the base of transistor 78. Transistor 78 then turns on, producing a collector current that flows into the base of transistor 72. Charge stored on capacitor 79 is supplied to the base of transistor 78, thereby reducing its turn-on time. When transistor 72 is on, the voltage at voltage supply node 61 is communicated to switch node 66. The presence of this voltage at switch node 66 causes a rapidly rising current to flow into the base of transistor 76 via resistor 80. As the emitter current of transistor 76 increases, the voltage drop across resistor 81 increases and capacitor 82 charges, raising the potential at node 83. The voltage at node 83 rises until the voltage drop between node 84 and node 83 is insufficient to hold transistor 76 on. As transistor 76 turns off, current flow through resistor 77 is blocked. Resistor 85 and resistor 86 quickly discharge the base-emitter junctions of transistors 72 and 78, respectively. The rapid turn-off of transistor 78 is also aided by Schottky diode 87, which prevents transistor 78 from saturating when on.

With transistor 72 off, the voltage at supply node 61 is no longer communicated to switch node 66. As the magnetic field in inductor 62 collapses, current is drawn through catch diode 65. The voltage at switch node 66 is thus reduced to a value one diode drop below ground. At this point the charge stored on capacitor 82 discharges via resistors 81 and 88. When the voltage at node 83 has fallen sufficiently, transistor 76 again turns on, repeating the cycle. In this manner, the circuitry of modulator 70 self-oscillates. A linear mode of operation is prevented due to the hysteresis supplied by resistor 80, which results in a voltage change at the base of transistor 76 of about 0.1 volt.

As noted above, the output voltage at modulator output 63 represents an average of the AC voltage present at switch node 66. Thus, if the duty-cycle of the voltage oscillations at node 66 is high, the DC output voltage at modulator output 63 will also be high. Similarly, if the duty-cycle is reduced, the output will decrease correspondingly. The duty-cycle of the oscillations produced by the circuitry of modulator 70 is determined by the voltage level of the control voltage signal applied to control input terminal 51. If the control voltage is relatively high, capacitor 82 will require a significant charging period before the voltage at node 83 rises sufficiently to turn off transistor 76. This produces a relatively large duty-cycle, as transistor 72 remains on for a longer period of time. If, however, the control voltage applied to control input terminal 51 is in the lower end of this range, transistor 76 does not remain on as long, or may not turn on at all. Thus, the DC output voltage delivered via modulator output 63 to inverter 55 may be steplessly selected within the voltage range between the voltage at ground terminal 65 and the voltage at voltage supply node 61 in response to the value of the control voltage at control input terminal 51.

Figure 9:
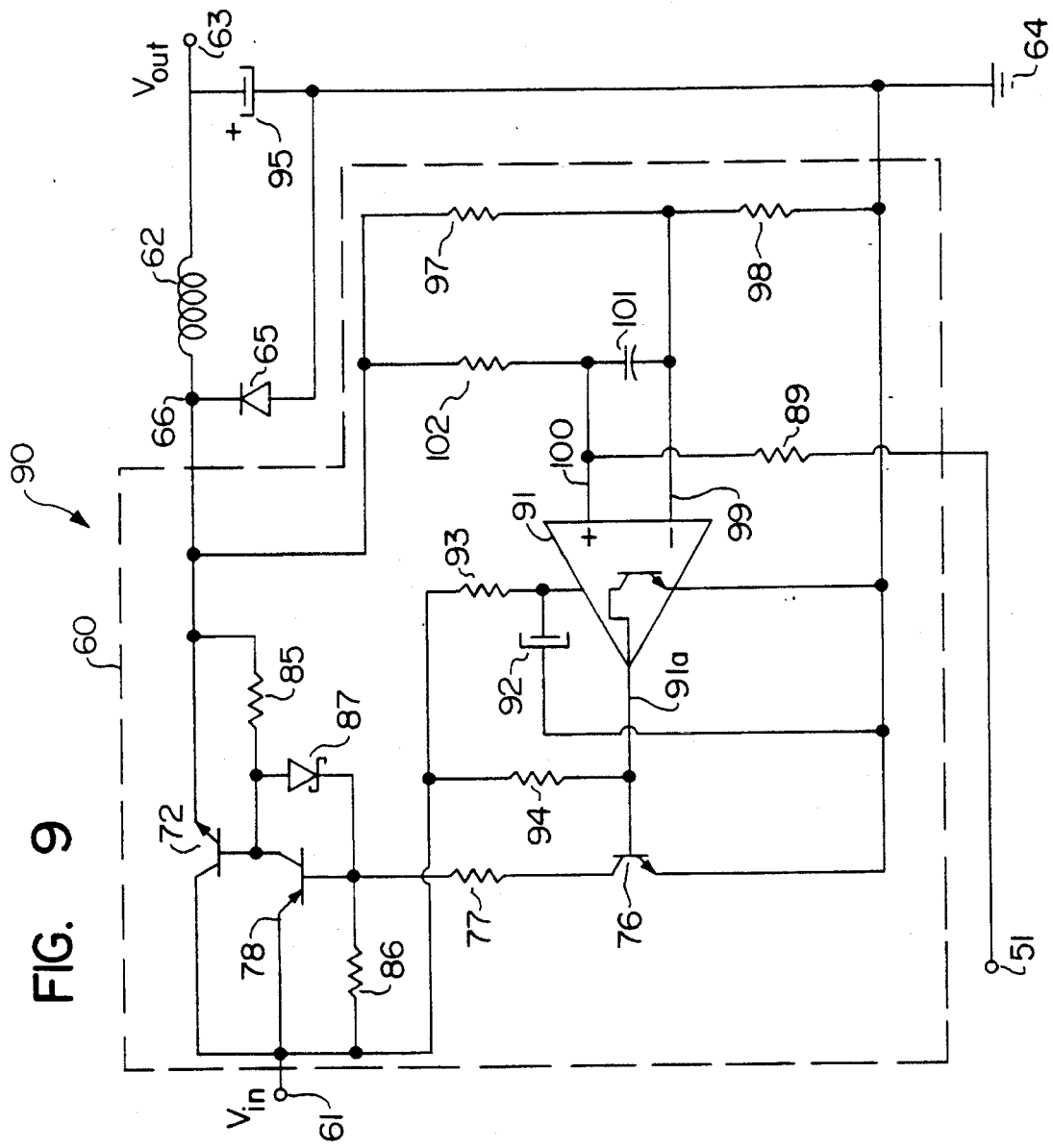
FIG. 9 is a detailed circuit diagram of a alternative embodiment of the modulator circuit of FIG. 7.

The circuitry of an alternative embodiment of modulator 52, modulator 90, is described with respect to FIG. 9. Modulator 90 includes comparator 91 to improve circuit stability over that achievable with the circuit of FIG. 8.

Comparator 91 is powered through a power supply filter, which includes power supply bypass capacitor 92 and decoupling resistor 93, to isolate comparator 91 from variations in the voltage at voltage supply node 61. Modulator 90 also has pull-up resistor 94 for transistor 76. Power output filter capacitor 95 further suppresses voltage ripples at modulator output 63.

The operation of modulator 90 is similar to that of modulator 70. When output 91$a$ of comparator 91 is high, current flows into the base of transistor 76, turning it on and allowing current to flow through resistor 77 and the base of transistor 78. When transistor 78 turns on, it produces a collector current that flows into the base of transistor 72, turning on transistor 72. The voltage at voltage supply node 61 is thus communicated to switch node 66. The presence of this voltage at switch node 66 causes voltage divider resistors 97 and 98 to supply a positive voltage at inverting input 99 of comparator 91.

As determined by the ratio of the resistances of resistors 97 and 98, the voltage supplied to inverting input 99 is larger than the control signal voltage supplied to non-inverting input 100 of comparator 91 from control input terminal 51 via resistor 89. Therefore, following the discharge of capacitor 101, the presence of a higher voltage at inverting input 99 than at non-inverting input 100 causes comparator 91 to output a low signal, turning off transistor 76. Resistor 102 provides hysteresis so that the voltage difference between inverting input 99 and non-inverting input 100 must exceed a threshold value before the output state of comparator 91 reverses, thus enhancing the stability of modulator 90.

Turn-off of transistor 76 interrupts current flow to the base of transistor 78, thus turning off transistors 78 and 72. Resistors 85 and 86 quickly discharge the base-emitter junctions of transistors 72 and 78 respectively. Rapid turn-off of transistor 78 is also aided by Schottky diode 87, which prevents transistor 78 from saturating when on.

For modulator 90, as for modulator 70, when transistor 72 is off, the voltage at supply node 61 is not communicated to switch node 66. As the magnetic field of inductor 62 collapses, current is drawn through catch diode 65. The voltage at switch node 66 is thus reduced to a value one diode drop below ground. When this occurs, the control voltage signal at control input terminal 51 exceeds the voltage supplied to inverting input 99 by voltage divider resistors 97 and 98. Following the discharge of capacitor 101 via resistor 98, comparator 91 again supplies a high output signal to transistor 76, repeating the cycle. The duty cycle of modulator 90 and thus the DC output voltage at modulator output 63 is controlled by the level of the voltage control signal at control input terminal 51. A higher voltage at input terminal 51 charges capacitor 101 to a greater extent during the period when transistor 72 is off. This greater charge causes a greater delay in switching comparator 91 from a high output state to a low output state, thus increasing the portion of the cycle when transistor 72 is on and the voltage at node 61 is being communicated to switch node 66. Accordingly, when the control signal is higher the DC output voltage at modulator output 63 is higher as well.

In a preferred embodiment of the present invention, inverter 55 is a two transistor, single transformer push-pull amplifier. Generator 53 is based on an integrated circuit square wave generator for providing a 0–12V gating square wave at 400 kHz. For instance, a 3825IC, available from Unitrode Integrated Circuits Corporation of Merrimac, New Hampshire may be used. The power supply voltage, which is provided to voltage supply node 61, is 30 VDC and ground terminal 64 is maintained at ground potential. Further, inductor 62 has an inductance of 280 µH, and diode 65 is a generic fast rectifying diode FR604. The voltage control signal applied to input terminal 51 ranges from 0–5V.

In the embodiment of modulator 70 of FIG. 8, transistor 72 is a PN 2SC3281 npn power transistor, available from Motorola Corporation, Schaumburg, Illinois, transistor 76 is a generic 2N2222 npn signal transistor, and transistor 78 is a Motorola PN 2SA1306B pnp power transistor. Capacitors 74, 75, 79 and 82 have capacitances of 1 µF, 220 µF, 0.03 µF, and 0.1 µF, respectively. Resistors 77, 80, 81, 85, 86, 88, and 89, have resistances of 1 KΩ, 62 KΩ, 100 Ω, 20 Ω, 120 Ω, 620 Ω and 1 KΩ, respectively. inductance of 18 µH and Schottky diode 87 is a generic 1N8519 and has a reverse breakdown voltage of 40V.

In a preferred embodiment of modulator 90 of FIG. 9, transistor 72 is a Motorola PN 2SC3281 npn power transistor, transistor 76 is a generic 2N2222 npn signal transistor, and transistor 78 is a Motorola PN 2SA1306B pnp power transistor. Capacitors 92, 95 and 101 have capacitances of 100 µF, 100 µF, and 0.1 µF respectively. Resistors 77, 85, 86, 89, 93, 94, 97, 98 and 102 have respective resistances of 1 KΩ, 27 Ω, 51 Ω, 1 KΩ, 100 Ω, 30 KΩ, 12 KΩ, 2 KΩ, and 300 KΩ. Schottky diode 87 is a generic 1N8519 and has a reverse breakdown voltage of 40V, and comparator 91 may be, for example, a type LM363, available from National Semiconductor Corporation, Santa Clara, Calif.

The embodiments of modulator 70 and modulator 90 provide a power supply having an efficiency of about 80% or more. This high efficiency results in a low power dissipation, allowing the power supply to produce a peak power of 750W while occupying a volume of approximately 8"×5"×2". Both modulator 70 and modulator 90 run "open loop" that is without the need for a feedback signal to stabilize the output.

The above-described power supplies provide a waveform having a output capable of providing a waveform at the electrodes of the surgical instrument having a voltage in the range of 10–130 VRMS, a crest factor less than 1.10, and a frequency preferably in the range of 400 kHz. These power supplies also have low output impedances, generally less than 20 ohms, and are capable of delivering up to 7 amperes of current (about 700W), depending upon the type of electrosurgical instrument being used and the specific operating conditions.

Because the circuitry of the present invention is "stiff" that is the output voltage does not vary significantly with respect to the load impedance encountered, no voltage feedback is required for the apparatus. Thus, unlike previously known electrosurgical generators wherein a voltage feedback signal is derived to regulate the output voltage, no such feedback circuitry is employed in the power supplies constructed in accordance with the principles of the present invention.

Figure 10:
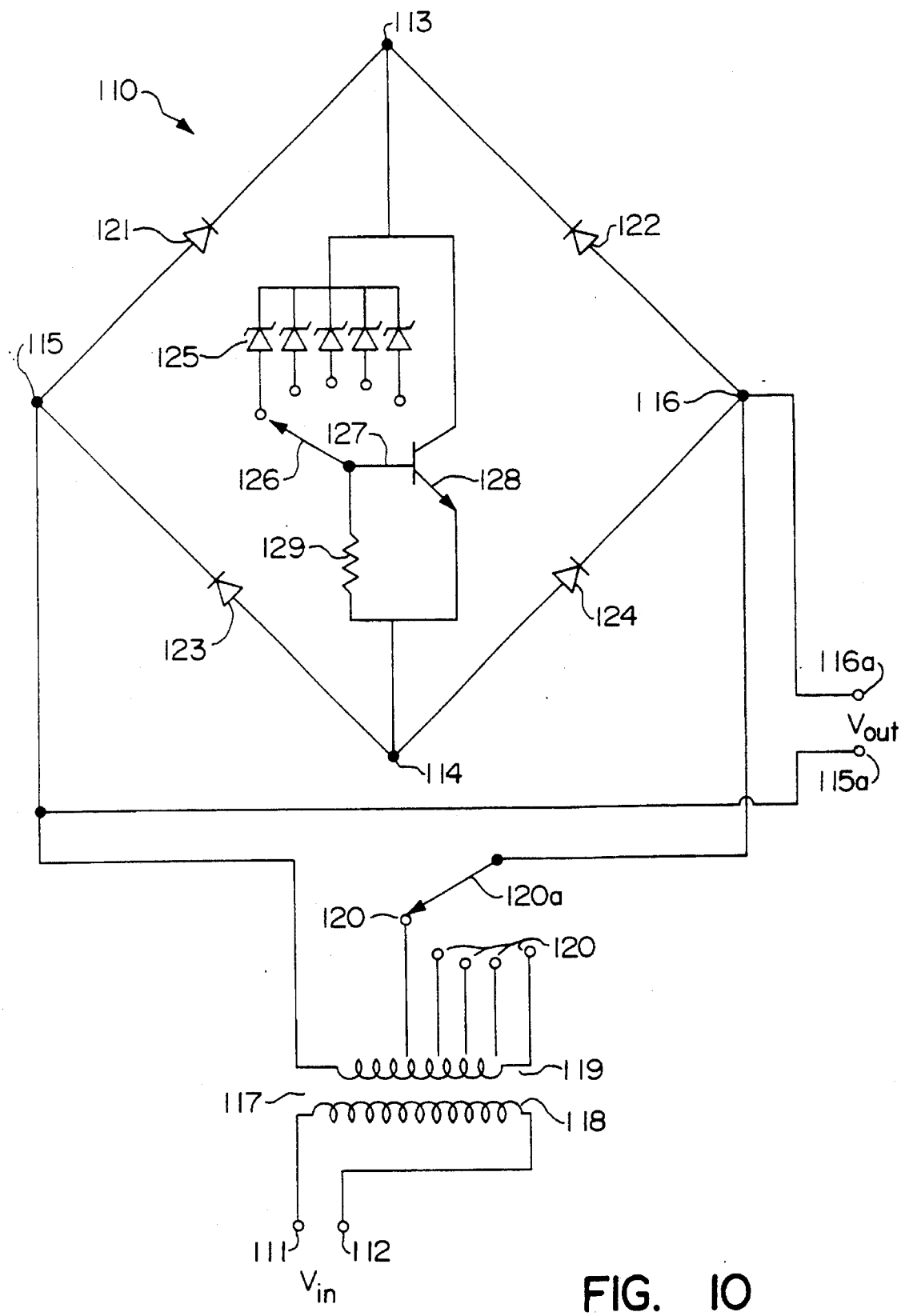
FIG. 10 is a circuit diagram for a retrofit device, for use with several previously known power supplies, for producing a power profile from those devices in accordance with present invention.

Referring now to FIG. 10, a retrofit circuit is described that enables several of the previously known electrosurgical generators listed in Table II to be used in accordance with present invention. Clipper circuit 110 of FIG. 10 is designed to be connected to, for example, the Neomed model 3000, to provide a power output in the regime discussed heretofore, namely, low voltage, high power voltage waveforms having a crest factor near unity. Clipper circuit 110 achieves this goal by "clipping" the peaks of the sinusoidal waveforms while reducing the output voltage of the conventional electrosurgical generator. Whereas the input waveform of the conventional electrosurgical generator has a pure sinusoidal shape, clipping circuit 110 supplies a constant voltage level to the electrosurgical instrument during that part of the waveform period so that the resulting output waveform has a crest factor near unity and generally less than 1.10.

Clipper circuit 110 also reduces the output impedance from the perspective of the attached electrosurgical instrument. Since impedance is proportional to the square of the voltage, the generally ten-fold reduction in output voltage (see Table II) from about 2000V to 200V also causes a 100-fold decrease in the impedance of the source. Accordingly, a conventional power supply having an output impedance of 400 ohms when connected to an electrosurgical instrument via clipping circuit 110 of the present invention, will appear to have an output impedance of only 4 ohms. Thus, the output voltage of a previously known electrosurgical generator retrofitted with clipper circuit 110 will not be subject to the impedance-matched voltage excursions discussed above with respect to FIGS. 2 and 3.

Clipping circuit 110 receives a high voltage AC input power signal at input terminals 111 and 112 from the output of a previously known electrosurgical generator, such as one of those shown in Table II, and provides low voltage low crest-factor AC output power at output terminals 115 and 116. The electrosurgical instrument is connected to output terminals 115a and 116a. The input signal is converted to the output signal by first adjusting the voltage downward to roughly the output level desired and second, clipping what is typically a sine wave signal near its peaks to produce a low crest-factor waveform. Because clipper circuit 110 uses polarity-sensitive elements—a transistor and diodes—the applied power must first be rectified to avoid reverse biasing these elements.

The input signal is stepped down to a lower peak-to-peak voltage level at nodes 115 and 116 by transformer 117. The voltage between nodes 115 and 116 is determined by the ratio between the number of windings on secondary 119 and the number of windings on primary 118. Preferably, multiple taps 120 are provided, each having a different secondary to primary ratio to accommodate various input voltage levels and therefore, various of the electrosurgical generators listed in Table II. The step-down ratio may therefore be adjusted by selecting the appropriate tap, for example, by switch 120a. If the voltage input signal is not stepped-down significantly, larger amounts of power will be dissipated during clipping, leading to a relatively low conversion efficiency for the retrofitted power supply, although this will produce a low crest-factor output. On the other hand, if a high step-down ratio is selected, little clipping will occur, resulting in a relatively high conversion efficiency, though the output signal will have a somewhat higher crest-factor.

In operation, the stepped-down AC waveform between nodes 115 and 116 is rectified by diodes 121, 122, 123 and 124. When the voltage at node 115 is higher than that at node 116, diodes 121 and 124 turn on, allowing the signal at node 115 to be passed to the nodes 113 and 114. For voltages below the breakdown voltage of the selected Zener diode 125, a little current is conducted to the base of transistor 128, which represents a high impedance between nodes 113 and 114. Thus, current flows primarily across output terminals 115a and 116a and the electrosurgical instrument and tissue disposed therebetween. No current flows through reverse biased diodes 122 and 123. When the polarity of the AC waveform shifts during the latter part of the waveform cycle, a low current passes through diodes 122, 123 and the peak clipping elements; no current then passes through reverse biased diodes 121 and 124.

The maximum output voltage provided between output terminals 115a and 116a is determined by selecting one of Zener diodes 125, each of which has a different breakdown voltage, with switch 126. When the voltage at node 113 rises to the Zener breakdown voltage (typically ranging from 30 to 100 volts) of the selected one of Zener diodes 125, current is conducted through this diode into base 127 causing transistor 128 to turn on. When on, transistor 128 provides a low impedance path from node 113 to node 114 than that across output terminals 115a and 116a. When transistor 128 is turned on, it acts to shunt current from the output terminals and prevents the voltage between terminals 115a and 116a from rising. If this voltage begins to rise, the selected one of Zener diodes 125 conducts additional current into base 127, further turning on transistor 128, thereby reducing its impedance and causing it to pass more current. The greater current flows then pulls voltage between terminals 115a and 116a lower.

Figure 11:
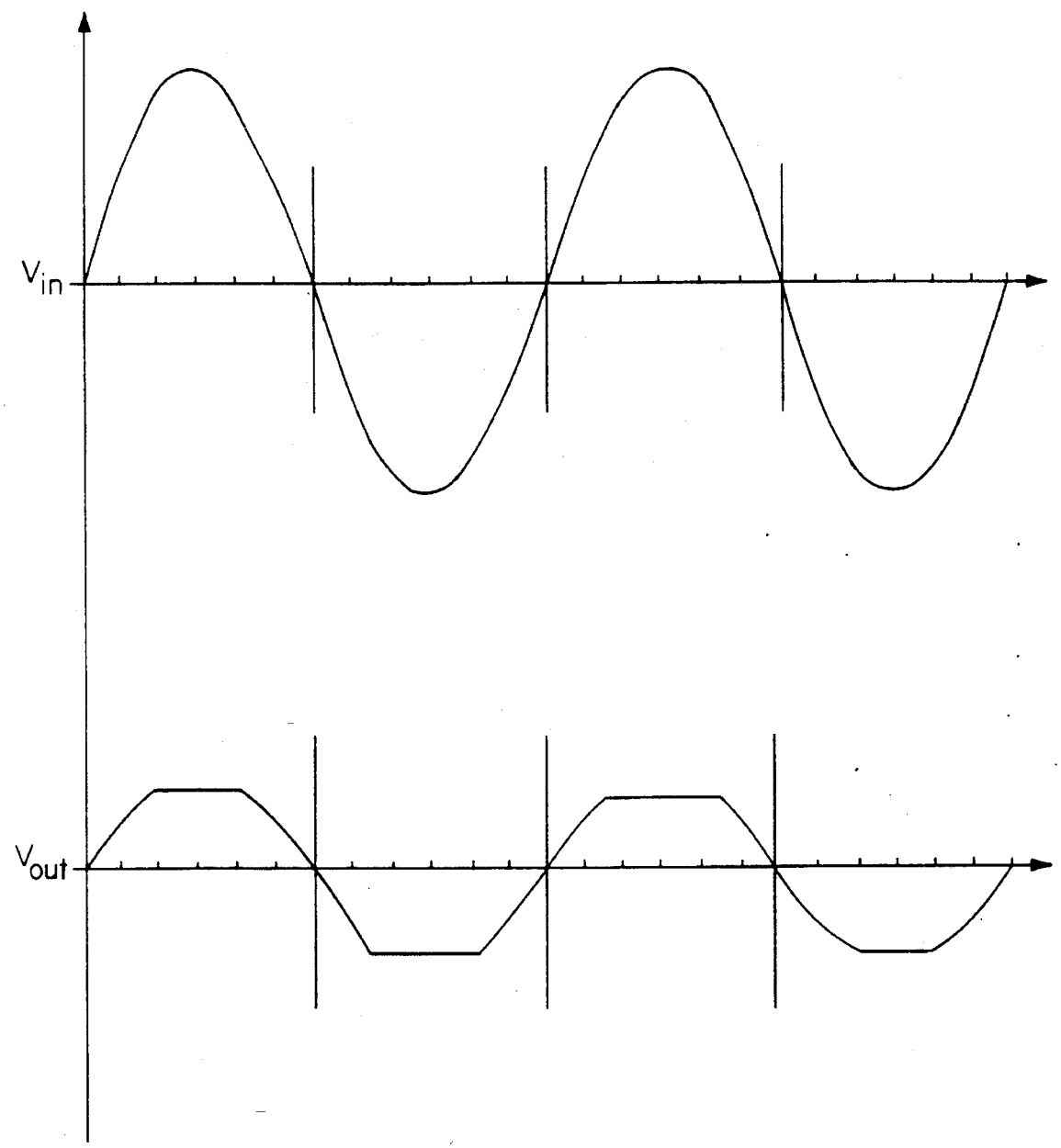
FIG. 11 shows a comparison of the input and output voltage waveforms obtained from the retrofit device of FIG. 10.

The voltage at output terminal 115a remains constant until later in the AC cycle, when the voltage at node 115, and therefore output terminal 113, falls. The selected one of Zener diodes 125 then ceases to conduct current into base 127, turning transistor 128 off. At this point, the emitter-base junction of transistor 128 discharges via resistor 129. Due to the symmetry of clipping circuit 110, when the voltage at node 116 rises to the Zener breakdown voltage, the voltage output at output terminal 116a is similarly clipped. The transformation of the input voltage waveform form the conventional electrosurgical generator to the output voltage waveform of the retrofit circuit is shown in FIG. 11.

In a preferred embodiment of clipping circuit 110, multiple taps 120 of transformer 117 have primary to secondary winding ratios in the range of 4:1 to 7:1, thus causing a factor of 4 to 7 reduction in voltage. Diodes 121, 122, 123 and 124 are rated at 6A and may be commonly packaged as a bridge rectifier. Transistor 128 is an npn transistor having a 20A capacity, such as PN 2SC3281 available from Motorola Corporation of Schaumburg, Ill. Resistor 129 has a resistance of 620 Ω.

It is contemplated that the methods of the present invention can be practiced using a conventional electrosurgical instrument (for example, the forceps or graspers of FIGS. 4 and 5), a conventional electrosurgical generator selected from the list provided in Table II, and a retrofit circuit constructed in accordance with the principles of the present invention, for example, clipping circuit 110. The retrofit circuit may then be coupled between the generator output and the electrosurgical instrument. While it is believed that this arrangement would provide satisfactory operation for some surgical procedures, it is nevertheless limited by the power output achievable by the conventional ES generator employed. For employing the Metzenbaum-style hemostatic scissors described in the above-mentioned U.S. patent application Ser. No. 07/877,703, filed May 1, 1992, the more robust power supply described heretofore with respect to FIGS. 7–9 would provide more satisfactory results.

One skilled in the art will appreciate that the present invention can be practiced by other than the described embodiments, which are presented for purposes of illustration and not of limitation, and the present invention is limited only by the claims that follow.

What is claimed is:

1. Electrosurgical forceps apparatus for manipulating tissue during surgery to cause hemostasis, the apparatus comprising:

first and second forceps members, each of the first and second forceps members having distal ends;

a pivot pivotally connecting the first and second forceps members together so that the distal ends of the first and second forceps members are selectively movable from an open to a closed position;

first and second electrodes disposed in opposition on the distal ends of the first and second forceps members;

a power supply that provides a constant voltage waveform to the first and second electrodes having a voltage less than 120 VRMS and a crest factor of about 1.1, to cause hemostasis without arcing or an accretion of coagulum on the first and second electrodes sufficient to interfere with the ability of the first and second electrodes to cause hemostasis; and means for connecting the power supply to the first and second electrodes.

2. Electrosurgical grasper apparatus for manipulating tissue during surgery to cause hemostasis, the apparatus comprising:

first and second grasper members, each of the first and second grasper members having proximal ends and distal ends;

a connecting plate disposed between the proximal ends of the first and second grasper members and to which the proximal end of each of the first and second grasper members are affixed, so that the distal ends of the first and second grasper members are selectively movable from an open to a closed position;

first and second electrodes disposed in opposition on the distal ends of the first and second grasper members;

a power supply that provides a constant voltage waveform to the first and second electrodes having a voltage less than 120 VRMS and a crest factor of about 1.1, to cause hemostasis without arcing or an accretion of coagulum on the first and second electrodes sufficient to interfere with the ability of the first and second electrodes to cause hemostasis; and means for connecting the power supply to the first and second electrodes.

3. A method of performing electrosurgery on tissue using a surgical instrument having an electrode for passing a high frequency current to the tissue to partially desiccate and cause hemostasis of the tissue, without arcing or an accretion of coagulum on the electrode sufficient to interfere with the ability of the electrode to cause hemostasis, the method comprising a series of steps comprised of:

(a) providing a surgical instrument having an electrode;

(b) connecting the electrode to an AC power supply;

(c) selecting and maintaining a constant output AC voltage waveform from the power supply at the electrode, wherein the voltage waveform is independent of the load impedance and has a crest factor of about 1.1;

(d) placing the electrode in electrical contact with the tissue so that high frequency current passes through the tissue to partially desiccate the tissue and cause hemostasis thereof by depositing a peak power in the tissue in excess of 50W, without arcing or an accretion of coagulum on the electrode sufficient to interfere with the ability of the electrode to cause hemostasis.

4. The method of claim 3 wherein it is desired to simultaneously cause hemostasis of and cut tissue, the surgical instrument including a mechanically sharp edge, the method further comprising the step of manipulating the surgical instrument to sever the partially desiccated tissue.

5. The method of claim 3 wherein heat is deposited in the tissue at a rate of between 50 and 700 watts.

6. The method of claim 3 wherein the step of selecting and maintaining the voltage waveform provides a voltage waveform at the electrode of the surgical instrument in the range of 10–120 VRMS.

7. The method of claim 3 wherein the voltage waveform is alternated with a frequency in a range of 100 kHz to 2 MHz.

8. The method of claim 3 wherein the step of selecting and maintaining a voltage waveform further comprises providing a power supply having an output impedance less than 20 ohms.

9. A method of performing electrosurgery on tissue using a surgical instrument having an electrode for passing a high frequency current to the tissue to partially desiccate and cause hemostasis of the tissue, without arcing or an accretion of coagulum on the electrode sufficient to interfere with the ability of the electrode to cause hemostasis, the method comprising a series of steps comprised of:

(a) providing a surgical instrument having an electrode;

(b) connecting the electrode to an AC power supply;

(c) selecting and maintaining a constant output AC voltage waveform from the power supply at the electrode, wherein the voltage waveform is independent of the load impedance and has a crest factor substantially less than 1.4;

(d) placing the electrode in electrical contact with the tissue so that high frequency current passes through the tissue to partially desiccate the tissue and cause hemostasis thereof by depositing a peak power in the tissue in excess of 50W, without arcing or an accretion of coagulum on the electrode sufficient to interfere with the ability of the electrode to cause hemostasis.

10. The method of claim 9 wherein it is desired to simultaneously cause hemostasis of and cut tissue, the surgical instrument including a mechanically sharp edge, the method further comprising the step of manipulating the surgical instrument to sever the partially desiccated tissue.

11. The method of claim 9 wherein heat is deposited in the tissue at a rate between 50 and 700 watts.

12. The method of claim 9 wherein the step of selecting and maintaining the voltage waveform provides a voltage waveform at the electrode of the surgical instrument in a range of 10–120 VRMS.

13. The method of claim 9 wherein the voltage waveform is alternated with a frequency in a range of 100 kHz to 2 MHz.

14. The method of claim 9 wherein the step of selecting and maintaining a voltage waveform further comprises providing a power supply having an output impedance less than 20 ohms.

* * * * *